United States Patent [19]

Rozakis

[11] Patent Number: 5,318,046
[45] Date of Patent: Jun. 7, 1994

[54] METHOD FOR CORNEAL REPROFILING

[76] Inventor: George W. Rozakis, 17886 Beach Rd., Lakewood, Ohio 44107

[21] Appl. No.: 949,440

[22] Filed: Sep. 23, 1992

[51] Int. Cl.$^5$ .............................................. A61B 17/00
[52] U.S. Cl. .................................... 128/898; 606/166
[58] Field of Search ........................... 606/166, 204.25; 128/898; 623/4, 5, 6

[56] References Cited

FOREIGN PATENT DOCUMENTS

| | | | |
|---|---|---|---|
| 3409798 | 10/1985 | Fed. Rep. of Germany ...... | 606/166 |
| 519191 | 6/1976 | U.S.S.R. .............................. | 606/166 |
| 1657180 | 6/1991 | U.S.S.R. .............................. | 606/166 |

*Primary Examiner*—Jerome L. Kruter
*Attorney, Agent, or Firm*—Fay, Sharpe, Beall, Fagan, Minnich & McKee

[57] ABSTRACT

A method of reshaping a cornea to meet the refractive needs of a patient is provided which includes: providing apparatus suitable for conducting keratomileusis in situ, the apparatus including a keratome means to cut across and remove a section of the cornea, and positioning means to maintain shaping means in register with respect to the cornea, the shaping means having a lower surface which can be brought into contact with the cornea, and engaged to downwardly depress the exposed surface of the cornea into a substantially flat configuration across a predefined optical zone; engaging the lower surface with the surface of the cornea, depressing the cornea and then causing the keratome to move across the cornea removing a predetermined section of the cornea thereby creating a revised exposed surface; retaining the section for later reattachment; providing a lenticular member having a predetermined thickness profile, and disposing the lenticular member between the lower surface and the revised surface of the cornea; engaging the lower surface to move downwardly depressing the lenticular member and thereby the revised surface of the cornea whereby the surface of the cornea is altered to a predetermined configuration converse to the configuration of the lenticular member, causing the keratome to move across the cornea a second time, removing a second predetermined section of the cornea; and, reattaching the first removed section.

17 Claims, 8 Drawing Sheets

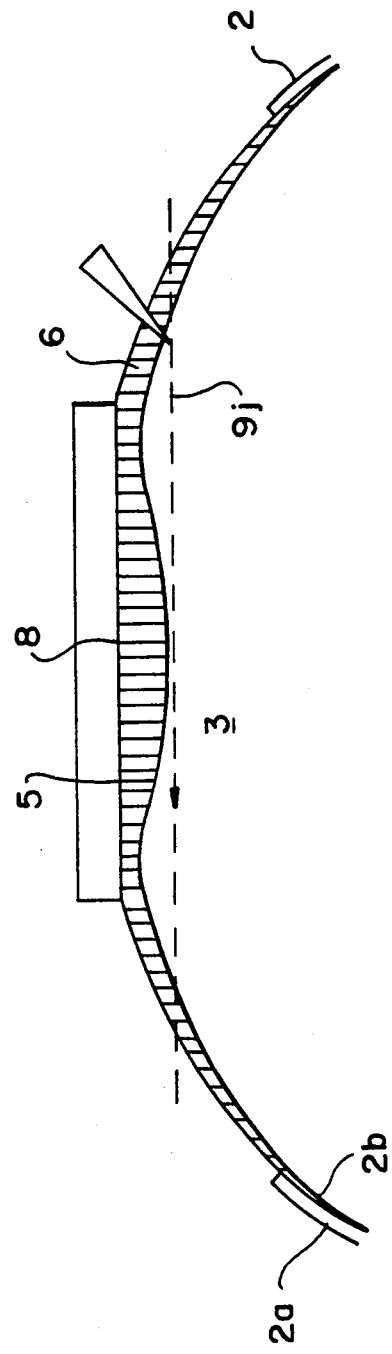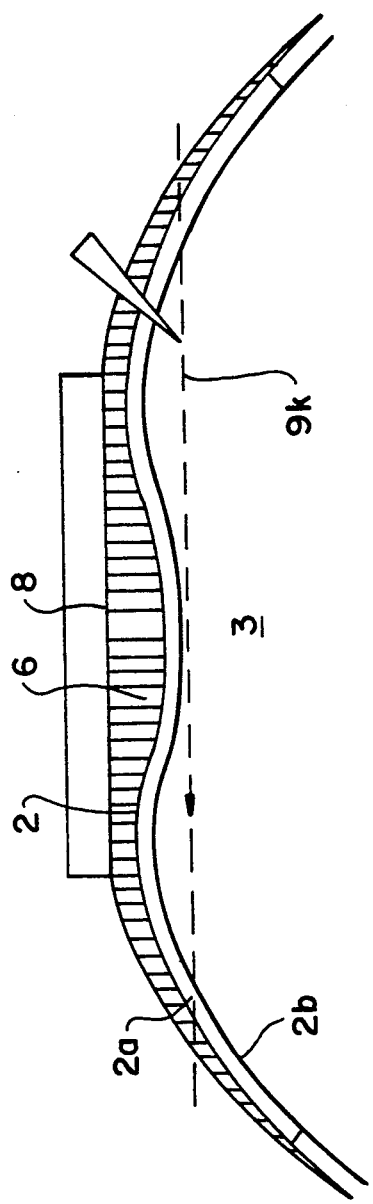

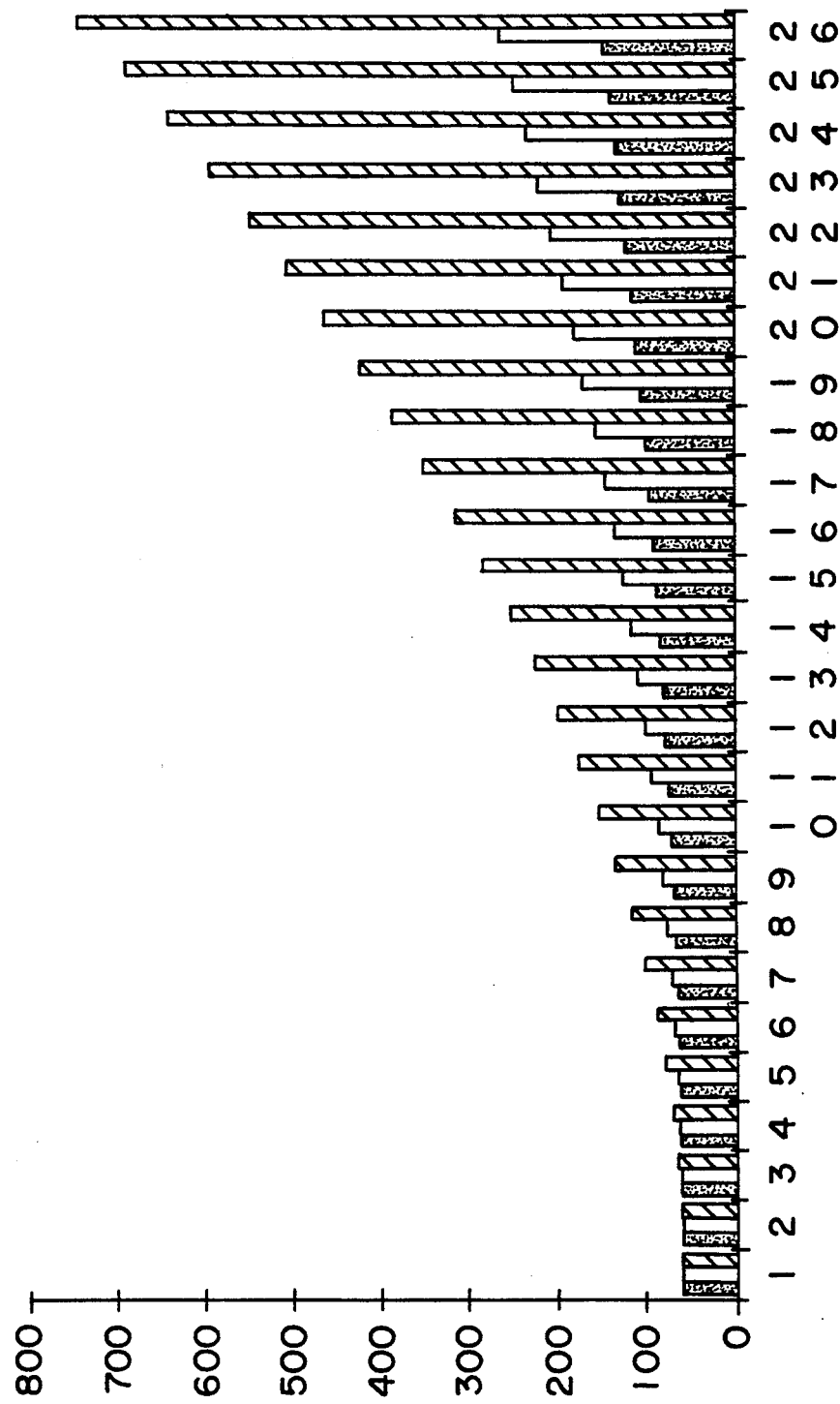

METHOD FOR CORNEAL REPROFILING

BACKGROUND OF THE INVENTION

This invention relates to the reprofiling of corneal surfaces and more particularly to a novel apparatus and method for facilitating the excising of a portion of the cornea having a particularly desired thickness profile.

Refractive surgery deals with those surgical procedures which change the focusing ability of the eye. The most basic of such techniques are quite old though efforts to modify and perfect them have been continuously underway. In general, the techniques developed to date have had increasing but not total success and consistency in the treatment of nearsightedness, but all of the techniques to date have had limited success in the surgical treatment of farsightedness, astigmatism, presbyopia and irregular astigmatism.

FIG. 1 diagrammatically illustrates a front view of the cornea designating areas A and B. Also designated are meridia C and D and the optical center of the cornea, point E. Refractive surgery deals with the curvature of the cornea. Corneas that are too steep can be thought of as inducing nearsightedness and corneas that are too flat cause farsightedness. Corneas with unequal curvatures such as along path C versus path D, similar to a football, cause regular astigmatism.

In the case of nearsightedness, the cornea is too steep which is the same as saying the radius of curvature is too small. Surgery involves flattening the cornea. These surgical methods either operate in the central cornea, area A or in the peripheral cornea, area B. In farsightedness, the cornea is too flat which is the same as saying the radius of curvature is too large, and here again surgical methods exist to steepen the cornea.

Presbyopia is a problem that develops in middle age in which the eye cannot focus at near if it sees clearly at distance. Patients who are farsightedness become presbyopic earlier in life. This is not a corneal problem but one of the lens inside the eye, however, it is theoretically possible to reshape the cornea surgically to produce a bifocal shape for both distance and near vision. Irregular astigmatism is a situation where curvatures along the cornea, as for example along meridia C and D are irregular, like a football with the air out of it. To date the most experience has been with nearsightedness correction as compared to farsightedness. Little data exists with respect to the treatment of presbyopia by making the cornea bifocal and no data exists, to our knowledge, to treat irregular astigmatism with corneal surgery.

Radial keratectomy is a relaxing procedure in which 90-95% depth radial cuts are made in the cornea in area B of FIG. 1, sparing a central optical zone of varying diameter. Drawbacks of this procedure include a limited range of correction, fluctuating vision, glare, and continued relaxation, leading to farsightedness, years after the procedure. Transverse incisions into the cornea in area B can be used to treat astigmatism.

Keratomileusis is also an old procedure which involves removing the anterior third of the cornea, freezing it, then placing it on a lathe. Layers of the cornea from the posterior surface of area A are then lathed away after which the reconfigured section is sutured back onto the cornea. This technique is useful for very high degrees of myopia and hyperopia.

Probably the most standard work on the subject of Keratomileusis is a Spanish language text "Queratomileusis-Querotofaquia" by Jose Barrequar who is considered one of the fathers of keratomileusis. Dr. Barrequar flatly states (pages 77-88) that attempts to depress the center of the cornea during keratomileusis will not work, and that the resulting excised section will merely be parallel to the original corneal section A more recent technique is excimer laser sculpting of the cornea. Here the corneal epithelium is scraped off to expose Bowman's membrane which covers the stroma. The Excimer laser then removes layers of cornea, including Bowman's membrane, in such a manner as to leave the curvature of the surface of the stroma changed, such that when the epithelium covers the stroma, the front curvature is different, thus correcting vision. This procedure suffers from slow, unpredictable healing at the epithelial-stromal interface caused by the absence of Bowman's membrane.

Another approach in excimer laser techniques of this type involves the use of an erodible mask such as is disclosed and claimed in U.S. Pat. No. 4,856,513 to Muller. In these techniques, the erodible material is placed between the Excimer laser beam and Bowman's membrane. As the laser is applied, it erodes through the mask, so that the laser quickly penetrates the mask at that point where it is thinnest, and the cornea under the thinner parts of the mask receives more exposure to the laser beam than the thicker portions. This, in turn, results in a different energy distribution on the cornea which, in turn, results in different cutting in different places and thus the refractive change. These techniques with the excimer laser are limited to nearsightedness and astigmatism particularly because of healing of the epithelium. The treatment of hyperopia has not proven successful because the epithelium tends to thicken and fill in attempts to steepen the cornea by excising less tissue centrally and more peripherally.

The most recent development is the use of a modified keratomileusis procedure, which may generally be described as keratomileusis in situ. This technique involves removing the anterior third of the cornea, after which a second cut of varying thickness, in an exact optical zone in the range of from about 3.5 to about 5.0 millimeters, is produced in the corneal bed, after which the piece which was originally removed is replaced. The missing portion removed from the corneal bed by the second cut results in a flattening of the corneal curvature and, thus, a correction of nearsightedness.

Keratomileusis in situ is described by Dr. Luis Ruiz whose apparatus and techniques are more particularly described in European Patent Application No. 90201166.7 (which has been published as Publication No. WO/0442156A1). As used herein, the terms "Ruiz Method" and "Ruiz Apparatus" shall be understood to mean the method and apparatus disclosed by Dr. Ruiz's European Patent Application No. 90201166.7, the drawings and specification of which are specifically incorporated herein by reference. Dr. Ruiz describes his apparatus as being made up of three main parts: a motor and transmission shaft assembly, a shaper head assembly, and a retaining ring assembly, the overall device being specifically designed to automatically perform corneal resections.

By causing the shaper head assembly to move automatically and smoothly at a constant speed across the retaining ring assembly which holds the eye in position for resection, precise uniform reproducible cuts are possible. In using the apparatus of Dr. Ruiz, the device is fitted over the cornea with the underside of the shaper head assembly depressing the surface of the cornea inwardly to an essentially flat configuration across a defined optical zone, and the keratome makes a first cut of about 160 microns. This cut is of essentially uniform thickness and is essentially parallel to the flattened corneal surface. The excised portion of the cornea is saved, the shaper head assembly is refitted over the eye, again in engagement with and flattening the surface of the cornea and a second smaller portion of exact diameter is removed from the corneal bed. The first excised section is then replaced over the cornea, and the second excised section is discarded.

The Ruiz Method is illustrated in FIG. 2a-i where a cornea, generally designated 1, has an anterior surface 2 comprised of layer of epithelium 21, upon Bowman's membrane 211. Numeral 3 designates what will be referred to as the corneal bed or 'stroma' through which the plane of resection will be located. In FIG. 2a the cornea is shown with reference to the underside surface 8 of the Ruiz shaper assembly, prior to engagement of the apparatus over the eye. FIG. 2b illustrates the elements of FIG. 2a after engagement showing corneal surface 2 flattened by underside surface 8 and showing dotted line 9 which is the cutting path of the keratome. FIG. 2c shows the cornea after the first keratome cut and FIG. 2d shows the portion of the cornea, designated 4, which was excised. FIG. 2e shows surface 8 reengaged for a second cut by the keratome along dotted line 9a in corneal bed 3. In general, the second cut is not as deep nor as large in diameter as the first cut. FIG. 2f shows the corneal surface after the second excising and FIG. 2g shows cornea 1 after the second excising and subsequent reattachment of first excised portion 4. Dotted line 9b designates the cut made in stroma to produce flattening of surface 2 as indicated. It should be noted that the flattening produced is extremely dependent upon the depth and importantly, the diameter of the resected piece. If the resected piece is too large, little effect is achieved because most of the resection is parallel to the original surface 2 whereas at smaller zones of resection, the resection is more lenticular and this results in flattening of the cornea.

While Dr. Ruiz suggests the potential use of his techniques for the correction of farsightedness as well as nearsightedness, he suggests doing so in a manner radically different from that in which it is normally employed in the correction of nearsightedness. This is so because the method of Dr. Ruiz cannot selectively remove tissue located more peripherally than centrally to steepen the bed. FIG. 2h shows the hypothetical cut, 9c, that Dr. Ruiz cannot produce to steepen the bed and thus steepen the corneal surface 2 once 4 is reapplied.

In attempting to correct farsightedness, Dr Ruiz makes a very deep cut with the keratome (about 75%), remove and then reapplies the excised portion. FIG. 2i shows the cut as 9d with back surface of the cornea 10. The first cut causes the remaining 25% of the cornea to bow out, in turn resulting in a steepening, the amount of steepening being determined by the diameter of the cut and the amount of bowing out which actually takes place. This technique is potentially dangerous and depends upon uncontrolled stretching of the cornea to achieve the desired steepening.

BRIEF DESCRIPTION OF THE DRAWINGS

FIGS. 3a-3e illustrates one embodiment of the process of the present invention employing a lenticule between the cornea surface and the underside surface of the cutting assembly.

FIG. 5 illustrates a side view of one embodiment of use of the lenticule of the present invention in conjunction with keratomileusis in situ.

FIG. 6 illustrates a side view of another embodiment of the use of the lenticule without the first cut of keratomileusis.

FIG. 9 illustrates a side view of one embodiment of use of the lenticule for myopia in conjunction with FIG. 6.

SUMMARY OF THE INVENTION

Figure 1:
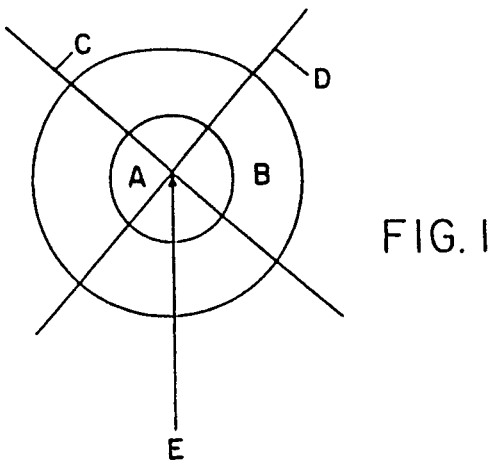
FIG. 1 is a diagrammatic illustration of a front view of cornea.

The present invention provides a method and apparatus for reprofiling corneal surfaces having utility in all forms of corneal recontouring, facilitating correction of near- and farsightedness, as well as astigmatism, the production of a bifocal cornea to treat presbyopia, and irregular astigmatism.

The apparatus, in addition to the Ruiz apparatus or similar keratectomy devices, comprises a curvilinear keratectomy lenticule having a predetermined thickness profile, said lenticule being adapted to be disposed between the cornea to be excised and the lower surface of the shaping or positioning means, one surface of the lenticule being in contact with said lower surface, and the opposed surface being in contact with, and inwardly depressing, the cornea. In the method of the present invention, when the microkeratome device is locked into position for excising a portion of the cornea, the lenticule will have effected a temporary recontouring of the cornea to facilitate excising a precisely contoured portion of the cornea.

Since the lenticule may also be cut when the keratome makes its cutting pass, the lenticule should desirably be essentially non-compressible and easily cut by the keratome while remaining exactly in place relative to the stroma; that is to say it must not move or impede the cutting action of the keratome as it excises the desired portion of the cornea. While the term non compressible has been used to describe the lenticule, in fact, the better term is resistant to compression, which shall be understood to mean that as used in the practice of the present invention, the lenticule is either not compressed, or is compressed in such a manner as to provide a defined reconfiguration of the corneal surface. A wide variety of materials may be employed in fabricating the lenticule, so long as they do not cause irritation of the eye when brought into contact with the eye. The preferred class of materials for fabrication of the lenticule would be thermoplastic or thermosetting polymer compositions, and materials of the type conventionally employed in fabrication of contact lenses.

THE PREFERRED EMBODIMENT OF THE INVENTION

The preferred method of the present invention is a method of reshaping a cornea to meet the refractive needs of a patient, and comprises the steps of providing an apparatus suitable for conducting keratomileusis in situ, the apparatus including a keratome to cut across and remove a section of the cornea, a shaping means to render the cornea flat and a positioning means to maintain the cornea in place, with respect to shaping means, the shaping means having a lower surface which can be brought into contact with the cornea, and engaged to downwardly depress the exposed surface of the cornea into a substantially flat configuration across a predefined optical zone; the lower surface is then engaged with the surface of the cornea, depressing the cornea so that when the keratome is moved across the cornea a predetermined essentially parallel section of the cornea is excised, thereby creating a revised exposed surface; the removed section being retained for later reattachment.

A lenticular member having a predetermined configuration, is then disposed between the lower surface of the shaping means and the revised surface of the cornea.

The lower surface of the shaping means depresses said lenticular member and thereby said revised surface of the cornea, whereby the surface of said cornea is altered to a predetermined configuration determined by the thickness, configuration, and compressibility of the lenticular member. The keratome is moved across the cornea a second time, removing a second predetermined section of the cornea and the first removed section is then reattached.

The novel lenticule temporarily reshapes the corneal surface to facilitate refractive surgery to the cornea. It has a predetermined three dimensional configuration or thickness profile, a resistance to compression and does not substantially impede the cutting action of the keratome.

The apparatus of the present invention involves an assembly for conducting keratomileusis in situ on a cornea, the assembly including a keratome means to cut across and remove one or more sections of the cornea, and positioning means to maintain a shaping means in place relative to said cornea, the shaping means having a lower surface which can be brought into contact with the cornea, and engaged downwardly to depress the exposed surface of the cornea into a substantially flat configuration across a predefined optical zone. The improvement comprises a lenticular member having a predetermined configuration disposed between the said lower surface and the surface of the cornea. When the lower surface is engaged to move downwardly, it depresses the lenticular member and thereby the surface of the cornea, causing the surface of the cornea to be altered to a predetermined configuration converse to the configuration of the engaged portion of the lenticular member, whereby when the keratome moves across the cornea it will remove a predetermined section of cornea bed which will, on relaxation of the positioning means, cause the cornea to have essentially the desired radii of curvature, the lenticule having a resistance to compression, and preferably no greater resistance than the cornea to the cutting action of a keratome.

Figure 2A:
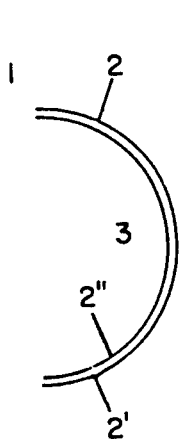
FIGS. 2a-2i illustrates the Ruiz process of the prior art.
Figure 2B:
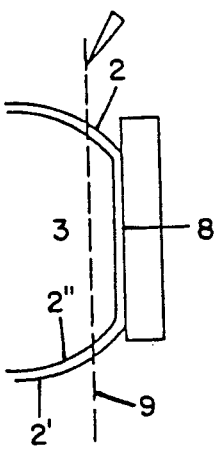
Figures 2C, 2D:
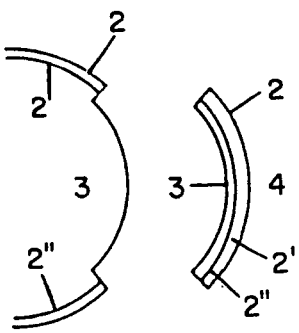
Figure 2E:
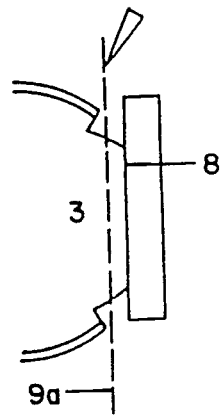
Figure 2F:
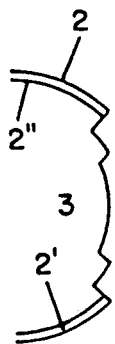
Figures 2G, 2H:
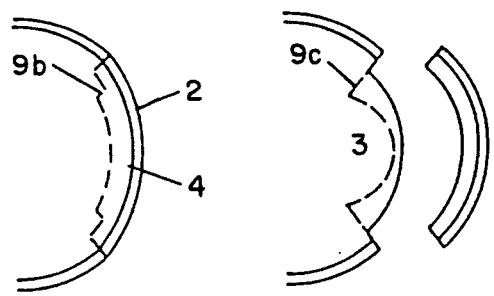
Figure 2I:
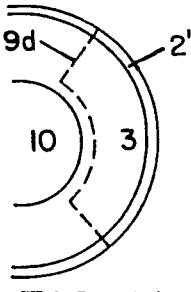
Figure 3A:
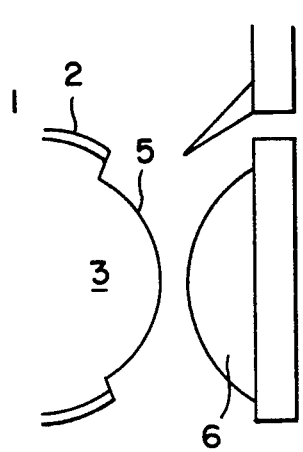
Figure 3B:
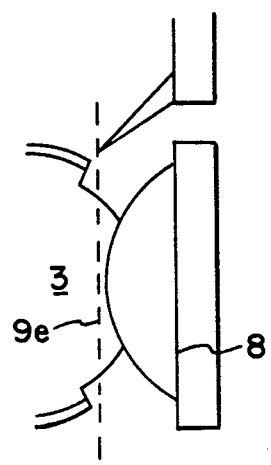
Figure 3C:
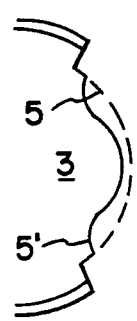
Figure 3D:
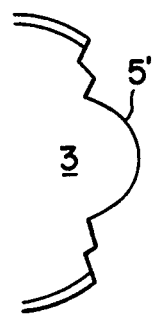
Figure 4E:
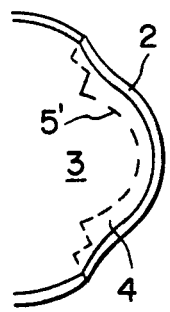
FIGS. 4a-4d illustrates another embodiment of the present invention.
Figure 4A:
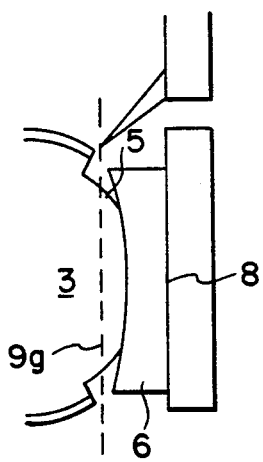
Figure 4B:
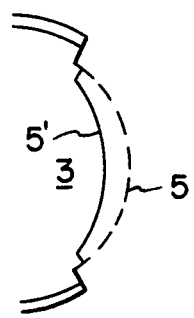
Figure 4C:
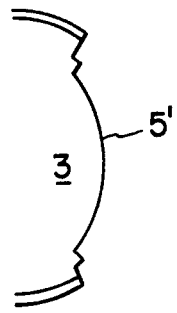
Figure 4D:
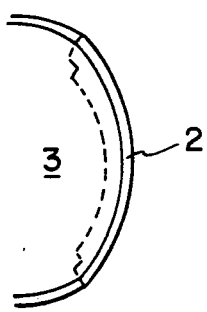

FIG. 3 illustrates one of the preferred embodiments of the method of the present invention in treating hyperopia. FIG. 3a shows the cornea after the first cut of the Ruiz procedure (and substantially corresponds to the cornea shown in shown FIG. 2c. As shown in FIG. 3a, the revised surface 5 of the cornea is aligned with lower surface 8, as in FIG. 2; however, lenticular means 6 is disposed between the lower surface and the revised surface, 5, of the cornea. FIG. 3b shows the same elements after the lower surface 8 has been downwardly engaged to depress the lenticular means 6 into the stroma, depressing and revising the surface 5. Dotted line 9e illustrates the cutting path of the keratome in the same manner as lines 9 and 9a of FIG. 2. FIG. 3c reveals the cut produced by the keratome in FIG. 3b, with surface 5 of FIG. 3b now shown as a dotted line, and the new surface is 5'. This cut would steepen the cornea and thus treat hyperopia. FIG. 3d shows a steeper corneal surface as compared to 3a and FIG. 3e shows a steepening of the ocular surface after reattachment of 4, described in respect to 2d and 2g.

FIG. 4 shows another embodiment of the present invention with the shaping assembly surface 8 pressing downward upon a concave lenticule 6 and a cut is made with the keratome along dotted line 9g. FIG. 4b shows the cornea after the cut and disengagement of the lower surface 8 and shows new revised surface 5' and also original revised surface 5 as a dotted line. Thus the excision results in a flattening of the corneal bed 3, as shown in FIB. 4b since more tissue is removed centrally and less peripherally. FIG. 4c shows the bed without dotted line 5 which defined the pre-excision contour. 5' defines the new surface contour created by keratome excision along line 9g in FIG. 4a. Upon reattachment of first cut 4 as described in 2g, the central cornea will be flatter as shown in FIG. 4d.

As illustrated in FIGS. 3 and 4, it will be clear that the process of the present invention is capable of excising any portion of the corneal bed by adjusting the thickness profile of the lenticule thereby facilitating correction of myopia, hyperopia, astigmatism, irregular astigmatism and also produce novel cuts to produce a bifocal cornea to treat presbyopia. Again, while FIGS. 3 and 4 are illustrative from a side view, it will, of course, be obvious that the contour of lenticule 6 can be adjusted to provide a greater depth of excising in a given area as opposed to other areas, that is to say, for example, along axis C or axis D of FIG. 1 to correct astigmatism.

FIG. 5 represents another illustration showing shaping means surface 8 depressing lenticule 6 which thus alters surface 5 into a predefined configuration thus permitting the keratome to cut a unique profile into corneal stroma 3 in this case treating hyperopia, as less is excised centrally and more peripherally. FIG. 5 illustrates the cut line as 9j which is shown to traverse the lenticule and the stroma.

FIG. 6 is similar to FIG. 5, but the lenticule is depressed against the original surface of the cornea as shown by epithelium 2a and Bowmans membrane 2b, that is to say, there has been no first excising step by the keratome to provide a revised surface as illustrated in FIG. 4 and FIG. 3a–e. In FIG. 6, shaping means surface 8 depresses lenticule 6 which depresses corneal surface 2 into a desired configuration so that when cut 9k is performed a precise thickness profile of anterior cornea is excised. While the embodiment illustrated in FIG. 6 is not the preferred embodiment of the present invention, it does provide results at least equivalent to those obtained by employing erodible mask laser techniques and other current techniques with the excimer laser. While the embodiment of FIG. 5 would suffer from the same healing limitations presented by the erodible mask laser techniques, it may provide substantially greater reproducibility and accuracy than are available with laser techniques.

Figure 7:
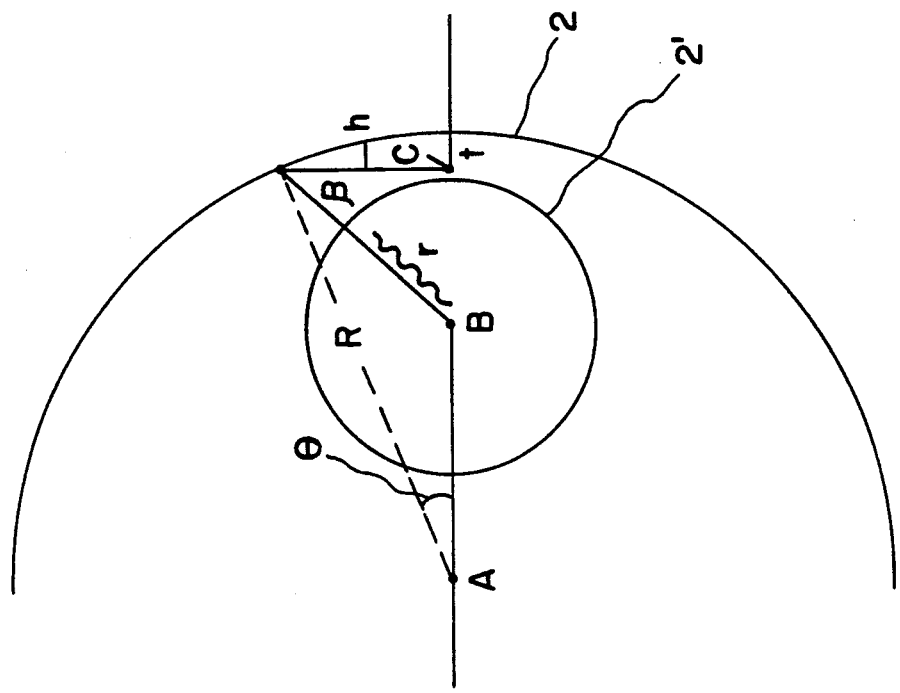
FIG. 7 illustrates a drawing from which mathematical relationships are derived to approximate the construction of a lenticule for myopia.
Figure 8:
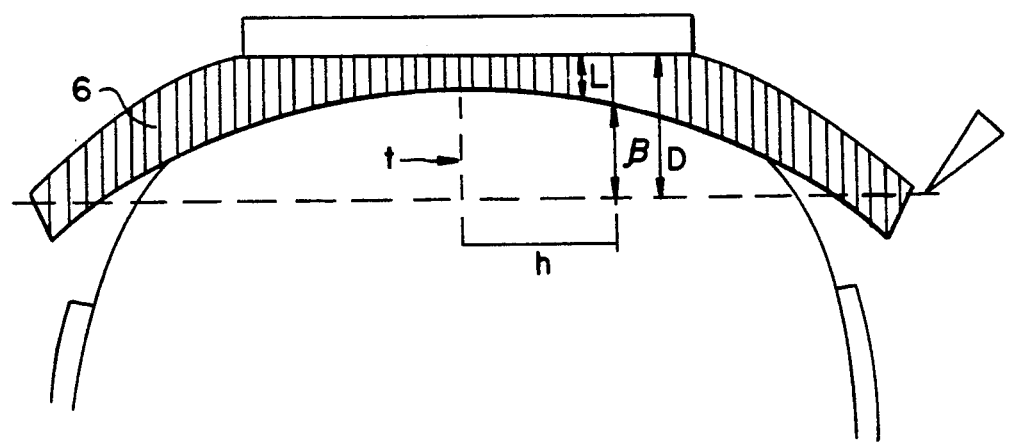
FIG. 8 illustrates a drawing from which mathematical relationships are derived to approximate the construction of a lenticule for hyperopia.

FIGS. 7, 8 and 9 and Table 1 define some of the parameters of measurement for determining the contour of the lenticule to be employed to achieve a desired amount of excision as a function of desired refractive correction. FIG. 7 shows two circles of different radii of curvature. The larger circle's radius is shown as 'R' and the smaller circle as 'r'. The larger circle represents the desired radius of curvature of the cornea after surgery has been performed. The smaller circle represents the preoperative cornea. In other words, 2 represents the surface of the cornea before surgery and 2' the surface after surgery. Therefore the excision to be produced must be that area between 2 and 2'. The Optical zone of correction is defined by the points at which the two circles intersect. Beta (B) approximates the distance that the keratome will cut when the shaping means has depressed the lenticule into the cornea surface. The mathematics are therefore designed to solve for B as a function of Theta. The mathematics used involve standard sine and cosine functions with right triangles, Pythagoreans theorem and the law of cosines.

With reference to the Figure, circle with center B has radius 'r'. Beta is always equal to 'alpha' minus the radius of curvature 'r', where alpha is the length of the line segment from B to the larger circle.

$$(Beta = r - alpha)$$

Since 'r' is known, solving for alpha will give Beta. Lower case letter 't' is the thickness of the cornea to be removed at the optical center of the eye previously designated as E in FIG. 1. Line segment AB is equal to $R + t - r$. Theta is the angle defined by the line segment AB and the radius originating at the circle with center at A. This is important later in the calculations.

$$AB = R + t - r$$

Now, using Pythagoreans theorem, $h^2 + (BC)^2 = alpha^2$ and we can see that $h = R^*\sin(theta)$ and $BC = R^*\cos(theta) - AB$. Since we know $AB = R + t - r$ then $BC = R^*\cos(theta) - (R + t - r)$. If we substitute into $h^2 + (BC)^2 = alpha^2$ these values and solve for alpha we arrive at:

$$alpha = SQRT \; [(R^*Sin(theta))^2 + (R^*Cos(theta) - (R + t - r))^2]$$

So Beta, the resection with the shaping means depressing the lenticule into the depressed cornea is approximated by:

$$Beta = r - SQRT \; [(R^*Sin(theta))^2 + (R^*Cos(theta) - (R + t - r))^2]$$

Now to determine the lenticule thickness we need to define the cut depth of the keratome as depth D. FIG. 8 shows beta when the shaping means surface 8 de-

TABLE 1

| | A | B | C | D | E | F |
|---|---|---|---|---|---|---|
| 1 | Preop K | 50.00 | | | | |
| 2 | Postop K | 40.00 | Line segment AB | 1750.00 | | |
| 3 | | | Preop 'r' | 6600.00 | Thetaoz | 0.30 |
| 4 | | | Postop 'R' | 8250.00 | OZ | 4.91 |
| 5 | | | Depth of Cut 'D' | 160.00 | | |
| 6 | | | central cut 't' | 100.00 | | |
| 7 | | | | | | |
| 8 | Theta degrees | Theta radians | BETA | h | 'L'enticule | |
| 9 | 0.00 | 0.00 | 100.00 | 0.00 | 60.00 | |
| 10 | 1.00 | 0.02 | 99.66 | 0.14 | 60.34 | |
| 11 | 2.00 | 0.03 | 98.65 | 0.29 | 61.35 | |
| 12 | 3.00 | 0.05 | 96.96 | 0.43 | 63.04 | |
| 13 | 4.00 | 0.07 | 94.59 | 0.58 | 65.41 | |
| 14 | 5.00 | 0.09 | 91.55 | 0.72 | 68.45 | |
| 15 | 6.00 | 0.10 | 87.84 | 0.86 | 72.16 | |
| 16 | 7.00 | 0.12 | 8.346 | 1.01 | 76.54 | |
| 17 | 8.00 | 0.14 | 78.42 | 1.15 | 81.58 | |
| 18 | 9.00 | 0.16 | 72.71 | 1.29 | 87.29 | |
| 19 | 10.00 | 0.17 | 66.34 | 1.43 | 93.66 | |
| 20 | 11.00 | 0.19 | 59.32 | 1.57 | 100.68 | |
| 21 | 12.00 | 0.21 | 51.64 | 1.72 | 108.36 | |
| 22 | 13.00 | 0.23 | 43.32 | 1.86 | 116.68 | |
| 23 | 14.00 | 0.24 | 34.35 | 2.00 | 125.65 | |
| 24 | 15.00 | 0.26 | 24.75 | 2.14 | 135.25 | |
| 25 | 16.00 | 0.28 | 14.52 | 2.27 | 145.48 | |
| 26 | 17.00 | 0.30 | 3.66 | 2.41 | 156.34 | |
| 27 | 18.00 | 0.31 | −7.82 | 2.55 | 167.82 | |
| 28 | 19.00 | 0.33 | −19.91 | 2.69 | 179.91 | |
| 29 | 20.00 | 0.35 | −32.60 | 2.82 | 192.60 | |
| 30 | 21.00 | 0.37 | −45.89 | 2.96 | 205.89 | |
| 31 | 22.00 | 0.38 | −59.77 | 3.09 | 219.77 | |
| 32 | 23.00 | 0.40 | −74.24 | 3.22 | 234.24 | |
| 33 | 24.00 | 0.42 | −89.27 | 3.36 | 249.27 | |
| 34 | 25.00 | 0.44 | −104.88 | 3.49 | 264.88 | | presses the lenticule 6 into the cornea 1. Depth of cut D is shown. Lenticule thickness L is shown and central thickness of cut t is shown. Also shown is the distance from the optical center, to beta, defined as distance 'h'. It is clear that D=beta+L or L=D-beta. Therefore if we wish to solve for the lenticular profile to produce a defined corneal excision we need to define a depth D, a central thickness cut t, the preoperative radius of curvature 'r'and Postoperative radius of curvature 'R'.

$$L=D-beta=D-(r-SQRT\ [(R*Sin(theta))^2+(R*Cos(theta)-(R+t-r))^2])$$

In order to determine the optical zone given by the above equation we need to define where the 2 circles intersect. That can be done using the law of cosines which dictates that, with reference to FIG. 7, r2=(AB)2+R2−2(AB)RCos(thetaOZ). ThetaOZ in this equation is one half of the optic zone and is determined by rearranging the equation to $$thetaOZ=arccos\ [(r^2-(AB)^2-R^2)/2(AB)R].$$

Now given the angle thetaOZ we can calculate the height h at the intersection of the two circles as R*sin(-thetaOZ). To determine the optical zone we double this so that optical zone is approximated by:

$$OZ=2*R*sin(thetaOZ).$$

Table 1 provides representative data for a 10 diopter correction to illustrate the above derivation. The Preoperative radius of curvature is 50 diopters which converts to an 'r' value of 6600 microns. The postoperative curvature is 40 diopters which converts to an 'R' value of 8250 microns. Theta is shown in degrees and radians. Depth of cut D is chosen to be 160 microns. Central cut 't' is chosen to be 100 microns. Line segment AB is calculated from 'R', 'r,' and central cut 't'. Beta is calculated from the equation described above as is the Lenticule thickness. The distance h from the center of the cornea is also noted and refers 'h' in FIG. 8. FIG. 9 shows three lenticular profiles for varying corrections of 5 diopters (black), 10 diopters (white) and 20 diopters (shaded).

Figure 10:
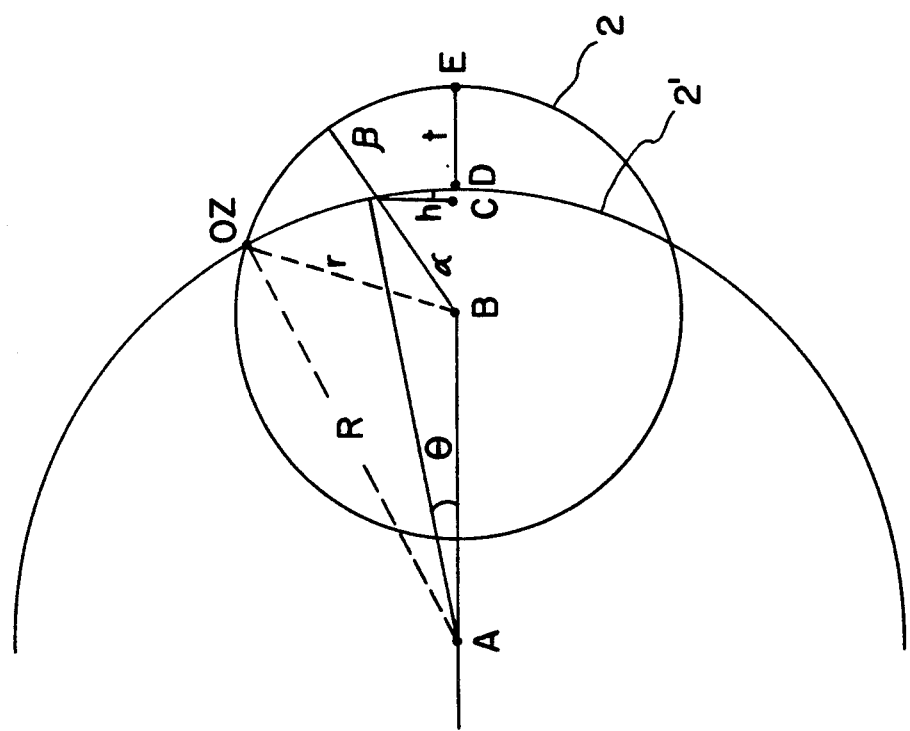
FIG. 10 illustrates one half of the profile of lenticules as derived from mathematical considerations derived from FIG. 7.
Figure 11:
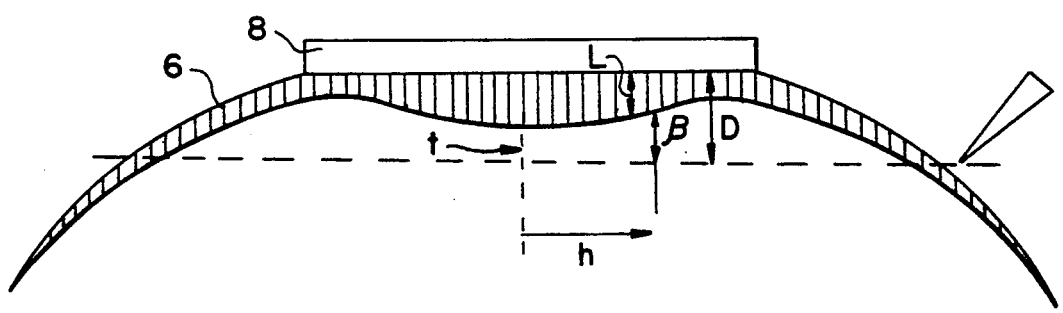
FIG. 11 illustrates a side view of one embodiment of use of the lenticule for hyperopia in conjunction with the mathematics derived from FIG. 10.
Figure 12:
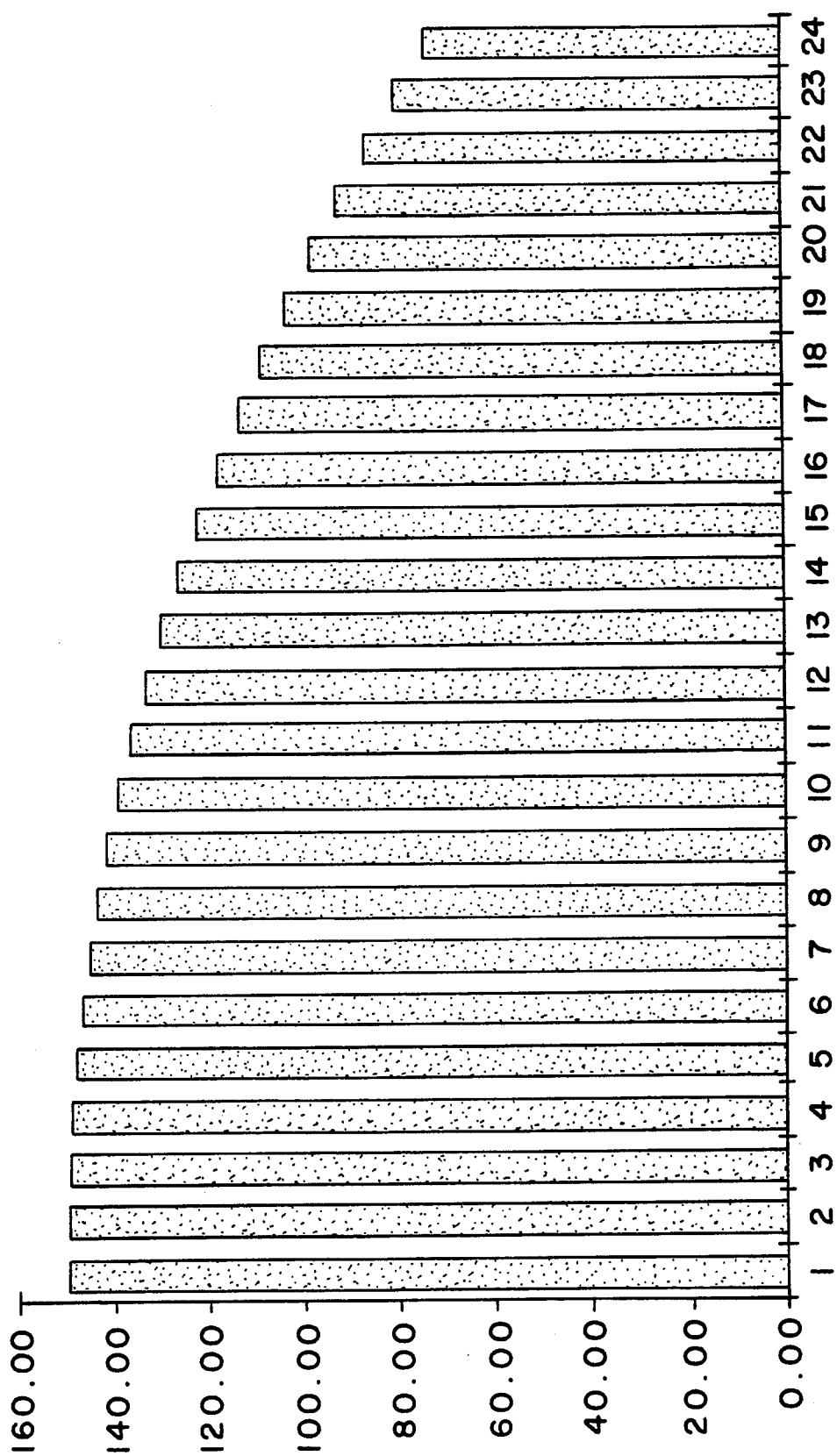
FIG. 12 illustrates a one half profile of one embodiment of a lenticule for hyperopia in conjunction with the mathematics derived from FIG. 10.

FIGS. 10, 11 and 12 and Table 2 show the correction of hyperopia. Here the preoperative surface is designated 2 and the postoperative surface 2'. The area between 2 and 2' needs to be excised to steepen the cornea. The distance Beta approximates the resected portion of cornea once the shaping means compresses the cornea and lenticule, and can be calculated. With reference to FIG. 10, 'R' is the preoperative corneal radius of curvature and 'r' the postoperative radius of curvature. 't' is the thickness of the cut at optical center point E of FIG. 1.

Segment $AB = R - r - t$
$'h' = R\sin(theta)$.
$BC = R\cos(theta) - AB$
$(r + beta)^2 = BC^2 + h^2$
substituting:

$$beta = \sqrt{(BC)^2 + h^2} - r$$

or $$beta = \sqrt{[(R\cos(theta) - (R - r - t))^2 + h^2]} - r$$

$$beta = [(R\cos(theta) - (R - r - t))^2 + h^2] - r$$

and
$L = $ Depth of cut minus beta

Table 2 shows a hyperopic correction of 5 diopters. Preop 'R' is 40 diopters or a radius of curvature of 8250 microns and postop 'r' is 45 diopters or a radius of curvature of 7333 microns. Depth of cut D is 200 microns and center cut 't' is 50 microns. AB segment is calculated to be 8150 microns. Theta is shown as radians in column B. The height 'h' to the point of treatment is shown in column C. Beta is calculated as from the above equation as is the lenticule. The optical zone size is shown as a function of theta in column F. FIG. 11 shows a schematic of this hyperopic lenticule which is thicker in the center. FIG. 11 also shows L, beta, h, t, lenticule 6, and shaping means 8. FIG. 12 shows the profile of the lenticule that produces a 5 diopter excision as based upon Table 2.

TABLE 2

| | A | B | C | D | E | F |
|---|---|---|---|---|---|---|
| 1 | Preop K | 40.00 | | | | |
| 2 | Postop K | 45.00 | AB segment | 8150.00 | | |
| 3 | | | Preop 'R' | 8250.00 | | |
| 4 | | | Postop 'r' | 7333.33 | | |
| 5 | | | Depth of Cut 'D' | 200.00 | | |
| 6 | | | center cut 't' | 50.00 | | |
| 7 | | | | | | |
| 8 | Theta | Radians | Height h | beta | Lenticule | OZ |
| 9 | 0.00 | 0.00 | 0.00 | 50.00 | 150.00 | 0.00 |
| 10 | 1.00 | 0.02 | 0.14 | 50.15 | 149.85 | 0.29 |
| 11 | 2.00 | 0.03 | 0.29 | 50.59 | 149.41 | 0.58 |
| 12 | 3.00 | 0.05 | 0.43 | 41.33 | 148.67 | 0.86 |
| 13 | 4.00 | 0.07 | 0.58 | 52.36 | 147.64 | 1.15 |
| 14 | 5.00 | 0.09 | 0.72 | 53.68 | 146.32 | 1.44 |
| 15 | 6.00 | 0.10 | 0.86 | 55.30 | 144.70 | 1.72 |
| 16 | 7.00 | 0.12 | 1.01 | 57.21 | 142.79 | 2.01 |
| 17 | 8.00 | 0.14 | 1.15 | 59.42 | 140.58 | 2.30 |
| 18 | 9.00 | 0.16 | 1.29 | 61.91 | 138.09 | 2.58 |
| 19 | 10.00 | 0.17 | 1.43 | 64.70 | 135.30 | 2.87 |
| 20 | 11.00 | 0.19 | 1.57 | 67.77 | 132.23 | 3.15 |
| 21 | 12.00 | 0.21 | 1.72 | 71.13 | 128.87 | 3.43 |
| 22 | 13.00 | 0.23 | 1.86 | 75.78 | 125.22 | 3.71 |
| 23 | 14.00 | 0.24 | 2.00 | 78.71 | 121.29 | 3.99 |
| 24 | 15.00 | 0.26 | 2.14 | 82.92 | 117.08 | 4.27 |
| 25 | 16.00 | 0.28 | 2.27 | 87.42 | 112.58 | 4.55 |
| 26 | 17.00 | 0.30 | 2.41 | 92.19 | 107.81 | 4.82 |
| 27 | 18.00 | 0.31 | 2.55 | 97.25 | 102.75 | 5.10 |
| 28 | 19.00 | 0.33 | 2.69 | 102.57 | 97.43 | 5.37 |
| 29 | 20.00 | 0.35 | 2.82 | 108.17 | 91.83 | 5.64 |
| 30 | 21.00 | 0.37 | 2.96 | 114.04 | 85.96 | 5.91 |
| 31 | 22.00 | 0.38 | 3.09 | 120.18 | 79.82 | 6.18 |
| 32 | 23.00 | 0.40 | 3.22 | 126.49 | 73.41 | 6.45 |

It will, of course, be understood that the parameters employed in calculating the amount of cornea to be excised and to define the desired lenticular configuration are presented by way of illustration and not by way of limitation. Particular conditions related to equipment or the desired excision, or even minor compressibility of the lenticule, may require different and/or additional parameters. In general, the data in Tables 1 and 2 illustrate one possible desired configuration for a lenticule to be used in correcting a cornea based on corneal curvature parameters, (preoperative corneal keratometric read and postoperative corneal keratometric reading), as set forth in the Tables.

In order to further evaluate the efficacy of the process and apparatus of the present, an experimental procedure was performed upon a cadaver eye. A lenticule was used similar in shape to that of lenticule 6 in FIG. 11 in that its central portion was thicker as compared to its peripheral portion. The experimental cornea was then engaged in the positioning means of the Ruiz apparatus, employing Ruiz plate 160 to provide a first excised portion having a thickness of 140 microns. The lenticule described above was then disposed between the revised surface of the experimental cornea and the lower surface of the shaping means of the Ruiz apparatus, the lower surface was engaged downwardly depressing the lenticular means into the revised surface of the experimental cornea depressing the revised surface downwardly. A second cut was then made with the keratome which passed through both the cadaver cornea and the lenticule. After the experimental cornea was disengaged from the retaining ring, it was examined and it appeared that the procedure had affected the desired excising such that a living human cornea would have expected to have its cornea steepened upon replacement of the first excised portion.

The most preferred lenticule will have one or more ribs projecting upwardly, away from the cornea, and adapted to engage one or more complementary channels in the positioning means. The positioning means of the Ruiz apparatus already has such a channel to permit vacuum fixation of the apparatus to the eye, and this channel could serve both functions.

The method of the present invention can be used to correct conditions wherein the eye suffers from a situation where the focusing of point rays of light are in front of the retina (myopia), posterior to the retina (hyperopia), behind the retina only during near visual tasks (presbyopia), contains two or more focal points in front of the retina (myopic astigmatism), two or more focal points behind the retina (hyperopic astigmatism), one focal point in front of the retina and one focal point behind the retina (simple astigmatism) or multiple focal points randomly scattered (irregular stigmatism). It should be noted however that the cornea is not the only cause of these problems since for example myopia may result because the cornea is too steep or the eye is too long—hyperopia because the cornea is too flat or the eye is too short. In spite of this corneal resculpting can provide correction.

In general it would seem that one would employ a lenticule which is convex as to treat hyperopia, and concave to treat myopia, and this can indeed be done. However, the more preferred lenticule has a generally concave configuration to facilitate placement over the eye. For hyperopia etc., the downward pushing force will be provided by the thickness profile of the lenticule which will render it effectively convex at the central portion of the lenticule.

This is illustrates by FIGS. 5 and 6 which show the lenticule to having an overall concave configuration, but a thickness profile which will provide greater depression at the optical center than at the optical periphery.

Figure 13:
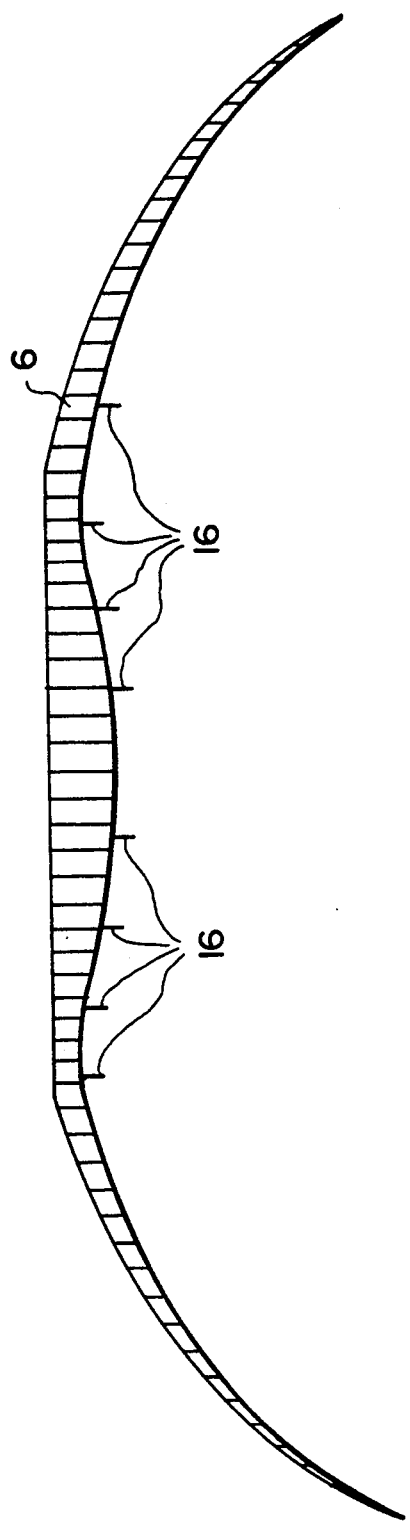
FIGS. 13 and 14 illustrate alternative embodiments having rib members to provide resistance to movement during passage of the keratome.
Figure 14:
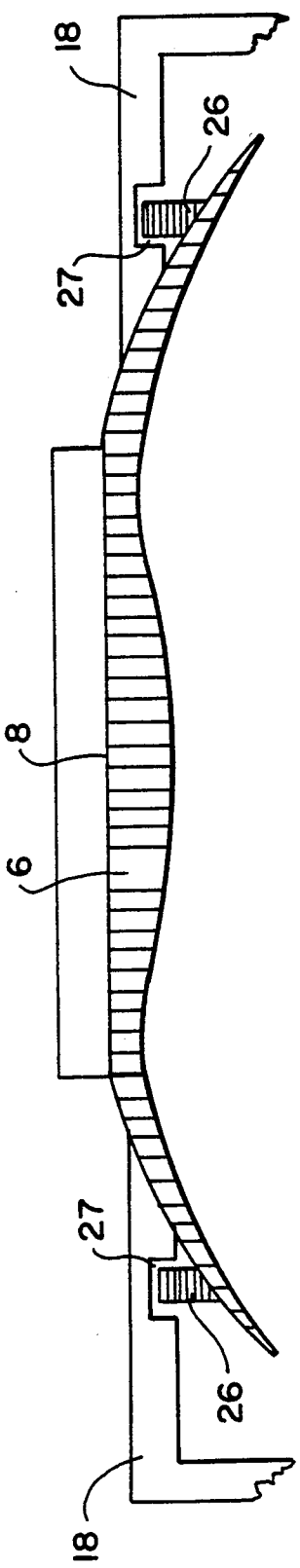

Indeed, the term lenticule is used in the broad sense, and includes not only those depicted in FIGS. 5 and 6, but even those where the center of the lenticule is a void, i.e. has no thickness, where an even deeper cut is to be made in the center of the cornea. It is also intended to include embodiments such as those of FIGS. 13 and 14. In the embodiment of FIG. 13, the lenticule 6 has a plurality of downwardly projecting rib members 16 which serve to frictionally engage the cornea to provide additional resistance to movement during the keratome pass. Ribs 16 may be simply downward projections or even radial ridges concentric with the optical center of the lenticule. In. FIG. 14, there is an upwardly projecting concentric ring 26 adapted to fit in channel 27 of positioning means 18. A lenticule could also have both types of positioning ribs 16 and 26. Resistance to movement can of course also be provided by using a setable adhesive material either in conjunction with the embodiments of F10, 13 or 14, or any of the other lenticule disclosed herein.

By adjusting the thickness profile of the lenticule, it is possible to provide corrections of a wide variety of conditions. As noted, to treat myopia the lenticule should have a profile where the center thickness is thinner relative to the peripheral thickness while to treat hyperopia the center thickness is thicker than the peripheral thickness. Similarly, to treat astigmatism the lenticule has two perpendicular axis with different thickness profiles intersecting at the center of the lenticule such that the axis having the thinner profile would be designed to be aligned over the axis or meridian of astigmatism so as to excise more cornea and thus treat the excessive steepness along that axis.

In the treatment of presbyopia the central portion of the lenticule may be designed to produce an aspherical surface either by leaving the cornea steeper relative to the more peripheral cornea, or alternatively, the central cornea can be left flatter relative to the peripheral cornea in either case providing an aspheric surface that is bifocal, or even multifocal. Either alternative would allow the patient distance correction, in one portion of the optical zone and near vision in the other portion of the optical zone. Thus the novel method and apparatus of the present invention can selectively provide a spherical or aspherical surface according to the refractive needs of the patient.

In the treatment of irregular astigmatism, one is dealing with a situation where there are essentially hills, bumps, and valleys everywhere, and you don't have any regularity. In this case a lenticule is custom fabricated to substantially match the irregular contour of the cornea so that when excision occurs the irregularities are neutralized thus rendering the surface in a final configuration as desired. In other words the lenticule is going to be thin where you want to cut off the hill, while where it is desirable to build up a valley one would make the lenticule thicker so as not to cut off as much in that area, so that overall net result is to provide the desirable surface. In essence one would have to define the irregularities and then custom design the lenticule to cut the hills and fill up the valleys, so that the surface of the lenticule in contact with the cornea would be essentially converse to the topography of the cornea.

In treating myopic astigmatism the lenticule should have a thickness profile not only to provide different cuts in different meridia, but also the overall cut should render the cornea flatter, thus the lenticule will have a thickness profile thinner at the center relative to the periphery. To treat hyperopic astigmatism, the central portion will always be thicker than the peripheral portions in both axis. To treat pure simple astigmatism, the central portion may be thinner than one peripheral thickness but thicker than the other peripheral thickness.

It will, of course, be obvious that the foregoing drawings and specification describe some, but not all, of the embodiments of the method and apparatus within the scope of the present invention and that the wide variety of alterations, changes, and substitutions can be made in the specific steps, methods, and materials hereinbefore disclosed without departing from scope of my invention. My intention to be limited only by the scope of the appended claims.

Having described the invention, the following is claimed:

1. A method of reshaping a cornea to meet the refractive needs of a patient, the steps which comprise: providing apparatus suitable for conducting keratomileusis in situ, said apparatus including a keratome means to cut across and remove a section of said cornea, and positioning means to maintain shaping means in register with respect to said cornea, said shaping means having a lower surface which can be brought into contact with said cornea, and engaged to downwardly depress the exposed surface of said cornea into a substantially flat configuration across a predefined optical zone;

engaging said lower surface with said surface of said cornea, depressing said cornea and then causing said keratome to move across said cornea removing a predetermined section of said cornea thereby creating a revised exposed surface;

retaining said section for later reattachment;

providing a lenticular member having a predetermined thickness profile, and disposing said lenticular member between said lower surface and said revised surface of said cornea; engaging said lower surface to move downwardly depressing said lenticular member and thereby said revised surface of said cornea whereby the surface of said cornea is altered to a predetermined configuration converse to the configuration of said lenticular member, causing said keratome to move across said cornea a second time, removing a second predetermined section of said cornea; and, reattaching said first removed section.

2. The method according to claim 1 wherein said lenticule has a thickness profile adapted to facilitate treatment of myopia.

3. The method according to claim 1 wherein said lenticule has a thickness profile adapted to facilitate treatment of hyperopia.

4. The method according to claim 1 wherein said lenticule has a thickness profile adapted to facilitate treatment of astigmatism.

5. The method according to claim 1 wherein said lenticule has a thickness profile adapted to facilitate treatment of irregular astigmatism.

6. The method according to claim 1 wherein said lenticule has a thickness profile adapted to facilitate treatment of presbyopia.

7. The method according to claim 6 wherein said lenticule has at least one rib at its outer periphery to enhance resistance to movement.

8. The method according to claim 7 wherein said rib is adapted to fit within a complimentary channel in said positioning means.

9. The method according to claim 7 wherein said second passage of said keratome cuts through both the stroma and a portion of said lenticule.

10. The lenticule according to claim 1 wherein said lenticule is fabricated from a thermoplastic plastic.

11. The lenticule according to claim 1 wherein said lenticule is fabricated from a thermosetting plastic.

12. The lenticule according to claim 1 wherein said lenticule has a configuration on one side thereof which can be engaged against a cornea to provide greater depression of the cornea at the optical center than at the optical periphery.

13. A method of reshaping a cornea to meet the refractive needs of a patient, the steps which comprise:

providing apparatus suitable for conducting keratomileusis in situ, said apparatus including a keratome means to cut across and remove a section of said cornea, said positioning means to maintain said cornea in place, positing means having a lower surface which can be brought into contact with said cornea, and engaged to downwardly depress the exposed surface of said cornea into a substantially flat configuration across a predefined optical zone;

providing a lenticular member having a predetermined configuration, and disposing said lenticular member between said lower surface and said surface of said cornea;

engaging said lower surface to move downwardly depressing said lenticular member and said surface of said cornea whereby the surface of said cornea is altered to a predetermined configuration converse to the configuration of said lenticular member; and, causing said keratome to move across said cornea and removing a predetermined section of said cornea.

14. The method according to claim 13 wherein said lenticule has at least one rib at its outer periphery to enhance resistance to movement.

15. The method according to claim 14 wherein said rib is adapted to fit within a complimentary channel means in said positioning means.

16. The lenticule according to claim 13 wherein said lenticule is fabricated from a thermoplastic plastic.

17. The lenticule according to claim 13 wherein said lenticule is fabricated from a thermosetting plastic.

* * * * *